United States Patent [19]

Berthold et al.

[11] Patent Number: 4,661,513
[45] Date of Patent: Apr. 28, 1987

[54] 3-AMINOPROPOXYPHENYL DERIVATIVES, THEIR PREPARATION AND PHARMACEUTICAL COMPOSITIONS CONTAINING THEM

[75] Inventors: Richard Berthold, Bottmingen, Switzerland; William J. Louis, 5 Von Nida Crescent, Rosanna, 13084 Victoria, Australia; André Stoll, Birsfelden, Switzerland

[73] Assignee: William John Louis, Victoria, Australia

[21] Appl. No.: 537,348

[22] Filed: Sep. 29, 1983

[30] Foreign Application Priority Data

Sep. 30, 1982 [CH] Switzerland ........................ 5758/82
Sep. 30, 1982 [CH] Switzerland ........................ 5761/82

[51] Int. Cl.[4] ..................... A61K 31/35; C07D 309/10
[52] U.S. Cl. .................................... 514/459; 549/425; 548/517; 514/422
[58] Field of Search ................ 549/425; 548/517; 424/283, 274; 514/459, 422

[56] References Cited

U.S. PATENT DOCUMENTS 4,425,362  1/1984  Berthold et al. .................... 514/486

FOREIGN PATENT DOCUMENTS 0052072  6/1982  European Pat. Off. .
85286  8/1983  European Pat. Off. .
1509527  5/1978  United Kingdom .

*Primary Examiner*—Nicky Chan
*Attorney, Agent, or Firm*—Sughrue, Mion, Zinn, Macpeak & Seas

[57] ABSTRACT

The compounds of formula I,

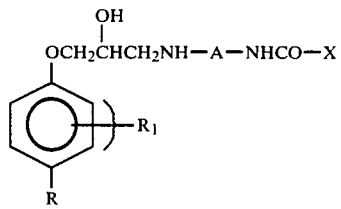

wherein the substituents have various significances, and physiologically hydrolyzable derivative thereof having at least one hydroxy group in esterified form, are useful as cardioselective $\beta$-adrenoceptor blocking and cardiotonic agents.

24 Claims, No Drawings

3-AMINOPROPOXYPHENYL DERIVATIVES, THEIR PREPARATION AND PHARMACEUTICAL COMPOSITIONS CONTAINING THEM

The present invention relates to 3-aminopropoxyphenyl derivatives, their preparation and pharmaceutical compositions containing them.

In accordance with the invention there are provided compounds of formula I,

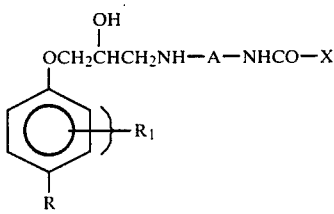

wherein
X is tetrahydropyranyl,
A is alkylene,
$R_1$ is hydrogen or a substituent and
R is hydrogen or a group $-Z-(CH_2)_n-Y-R_2$
wherein
$R_2$ is hydrogen, alkyl, alkenyl, cycloalkyl, cycloalkyl alkyl or an optionally substituted aryl, aralkyl or aralkenyl substituent,
Y is an oxygen or a sulfur atom and
either Z is an oxygen atom and n is 2 or 3 or Z is a bond and n is 1, 2 or 3 and physiologically hydrolyzable derivatives thereof having at least one hydroxy group in esterified form, hereinafter referred to as "the compounds of the invention".

"Alkylene" only comprises radicals having a carbon chain of at least 2 carbon atoms separating X from the nitrogen atom of the 3-aminopropoxy side chain.

In accordance with the invention there are especially provided compounds of formula Ia,

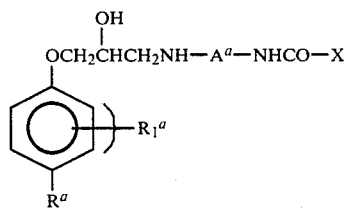

wherein
X is as defined above,
$A^a$ is alkylene of 2 to 5 carbon atoms and
$R_1^a$ is hydrogen, hydroxy, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, pyrrol-1-yl, cyano, carbamoyl, alkenyl of 2 to 5 carbon atoms, alkenyloxy of 3 to 5 carbon atoms wherein the double bond is not attached to the carbon atom adjacent to the oxygen atom, alkanoyl of 2 to 5 carbon atoms, nitro, amino, alkanoylamino of 1 to 5 carbon atoms or alkoxycarbonylamino of 1 to 4 carbon atoms in the alkoxy moiety thereof and $R^A$ is hydroxy or a group $-Z-(CH_2)_n-Y-R_2^a$
wherein
Z, n and Y are as defined above and
$R_2^a$ is hydrogen, alkyl of 1 to 5 carbon atoms, alkenyl of 3 to 5 carbon atoms wherein the double bond is not attached to the carbon atom adjacent to Y, cycloalkyl of 5 to 7 carbon atoms, cycloalkylalkyl of 3 to 7 carbon atoms in the cycloalkyl moiety and of 1 to 4 carbon atoms in the alkyl moiety thereof, or phenyl, phenylalkyl of 7 to 10 carbon atoms or phenylalkenyl of 9 to 11 carbon atoms wherein the double bond is not attached to the carbon atom adjacent to Y, the last three substituents optionally being mono- or independently di- or independently trisubstituted in the phenyl ring by alkyl of 1 to 4 carbon atoms, alkoxy of 1 to 4 carbon atoms or halogen of atomic number of from 9 to 35, and physiologically hydrolyzable derivatives thereof having at least one hydroxy group in esterified form.

A physiologically hydrolyzable derivative is a derivative in which under physiological conditions a hydroxy group in esterified form is split to the corresponding hydroxy group in unesterified form.

A group of derivatives in esterified form of the compounds of formula I is e.g. the compounds of formula E,

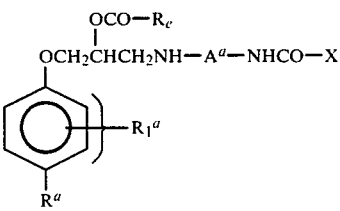

wherein
$R^a$, $R_1^a$, $A^a$ and X are as defined above and
$R_e$ is alkyl of 1 to 12 carbon atoms, cycloalkyl of 3 to 7 carbon atoms, phenyl, phenylalkyl of 7 to 12 carbon atoms, or phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

In another group $R^a$ is

wherein $R_e$ is as defined above. In another group $R^a$ is $-Z-(CH_2)_nOCOR_e$ wherein Z, n, and $R_e$ are as defined above. In another group $R_1^a$ is

wherein $R_e$ is as defined above.

Preferred are the compounds of the invention wherein any hydroxy group is in unesterified form.

Any monosubstituted phenyl ring appearing in or as a substituent preferably is substituted in the para position. Any disubstituted phenyl ring preferably is substituted in the meta and para positions. Any trisubstituted phenyl ring preferably is substituted in the meta, meta, para positions. Any phenyl ring preferably is unsubstituted, mono- or disubstituted. Any polysubstituted phenyl ring substituent preferably is substituted by identical substituents.

Alkyl of 1 to 4 carbon atoms and/or alkoxy of 1 to 4 carbon atoms and/or alkylthio of 1 to 4 carbon atoms preferably are of 1 or 2 carbon atoms, especially of 1 carbon atom. Alkyl of 1 to 5 carbon atoms preferably is of 3 or 4 carbon atoms, especially of 3 carbon atoms; it preferably is propyl. Halogen of atomic number of from 9 to 35 or of from 9 to 53 preferably is chlorine or bromine, especially bromine. Cycloalkyl of 3 to 7 carbon atoms preferably is of 3, 5 or 6 carbon atoms, especially 5 or 6 carbon atoms. Cycloalkyl of 5 to 7 carbon atoms preferably is of 5 or 6 carbon atoms, especially of 6 carbon atoms. Alkenyl of 2 to 5 carbon atoms preferably is of 2 or 3 carbon atoms, it especially is allyl. Alkenyl of 3 to 5 carbon atoms preferably is of 3 carbon atoms; it especially is allyl. Alkenyloxy of 3 to 5 carbon atoms preferably is of 3 or 4 carbon atoms; it especially is allyloxy. Cycloalkylalkyl of 3 to 7 carbon atoms in the cycloalkyl moiety and 1 to 4 carbon atoms in the alkyl moiety thereof is especially of 3, 5 or 6 carbon atoms in the cycloalkyl moiety and especially of 1 or 2 carbon atoms in the alkyl moiety thereof; it preferably is cyclopropylmethyl. Phenylalkyl of 7 to 10 carbon atoms preferably is of 7 or 8 carbon atoms; it especially is benzyl. Phenylalkenyl of 9 to 11 carbon atoms preferably is of 9 carbon atoms; it especially is cinnamyl. Alkanoylamino of 1 to 5 carbon atoms preferably is of 2 or 3 carbon atoms; it especially is acetamido. Alkanoyl of 2 to 5 carbon atoms preferably is of 2 or 3 carbon atoms; it especially is acetyl. Alkoxycarbonylamino of 1 to 4 carbon atoms in the alkoxy moiety thereof preferably is of 1 or 2 carbon atoms in the alkoxy moiety; it especially is methoxycarbonylamino. Alkylene of 2 to 5 carbon atoms preferably is ethylene. When it is of more than 2 carbon atoms, then it preferably is trimethylene or a moiety branched in the α position such a

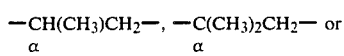
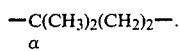

$R^a$ preferably is a group $-Z-(CH_2)_n-Y-R_2^a$.

$R_1^a$ preferably is in the position on the phenyl ring ortho to the 3-aminopropoxy side chain. It preferably is hydrogen, hydroxy, cycloalkyl, cyano, carbamoyl, halogen, alkenyl or alkenyloxy, especially hydrogen, hydroxy, cyano or halogen, especially hydrogen or halogen, particularly hydrogen.

$R_2^a$ preferably is alkyl, cycloalkylalkyl or optionally substituted phenylalkyl, especially alkyl or cycloalkylalkyl, especially cycloalkylalkyl. When it is optionally substituted phenyl, phenylalkyl or phenylalkenyl, it preferably is unsubstituted or monosubstituted. When the phenyl ring is substituted, it preferably is substituted by alkoxy.

X preferably is tetrahydropyran-3- or -4-yl, especially -4-yl.

Y preferably is an oxygen atom.
Z preferably is an oxygen atom.
n preferably is 2.

A preferred group of compounds of the invention is the compounds of formula I′

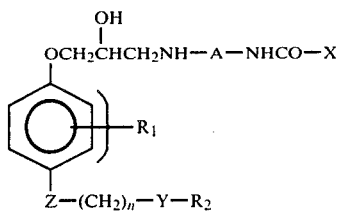

wherein A, X, Y, Z, n, $R_1$ and $R_2$ are as defined above, and physiologically hydrolyzable derivatives thereof having at least one hydroxy group in esterified form.

A particularly preferred group of compounds of the invention is the compounds of formula I′a

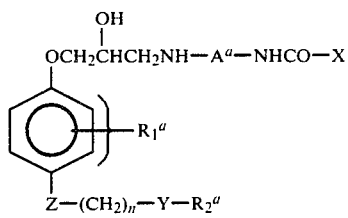

wherein $A^a$, X, Y, Z, n, $R_1^a$ and $R_2^a$ are as defined above, and physiologically hydrolyzable derivatives thereof having at last one hydroxy group in esterified form.

In a subgroup $R_2^a$ is hydrogen, alkyl of 1 to 4 carbon atoms, alkenyl of 3 to 5 carbon atoms wherein the double bond is not attached to the carbon atom adjacent to Y, cycloalkyl of 5 to 7 carbon atoms or cycloalkylalkyl of 3 to 7 carbon atoms in the cycloalkyl moiety and of 1 to 4 carbon atoms in the alkyl moiety thereof. In another subgroup $R_1^a$ is hydroxy.

Another group of compounds of the invention is the compounds of formula I″

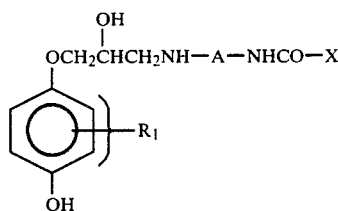

wherein A, $R_1$ and X are as defined above,
and physiologically hydrolyzable derivatives thereof having at least one hydroxy group in esterified form.

In a subgroup A has the significance indicated above for $A^a$ and $R_1$ has the significance indicated above for $R_1^a$.

Another group of compounds of the invention is the compounds of formula Ias,

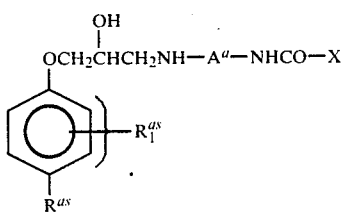

wherein

X and $A^a$ are as defined above and $R_1^{as}$ is hydrogen, halogen of atomic number of from 9 to 53 or cyano and $R^{as}$ is hydroxy or a group $-Z-(CH_2)_n-O-R_2^{as}$ wherein Z and n are as defined above and $R_2^{as}$ is alkyl of 1 to 5 carbon atoms, cycloalkyl of 5 to 7 carbon atoms or cycloalkylalkyl of 3 to 7 carbon atoms in the cycloalkyl moiety and of 1 to 4 carbon atoms in the alkyl moiety thereof.

In a subgroup $R_1^{as}$ is as defined above and $R^{as}$ is a group $-Z-(CH_2)_n-O-R_2^{as}$ wherein Z, n and $R_2^{as}$ are as defined above. In another subgroup $R_1^{as}$ is hydrogen and $R^{as}$ is hydroxy.

Another group of compounds of the invention is the compounds of formula Ipa,

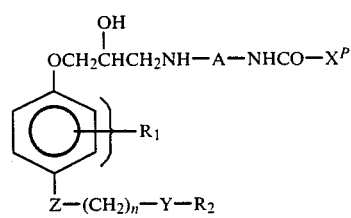

wherein

A, Y, Z, n, $R_1$ and $R_2$ are as defined above and $X^p$ is tetrahydropyran-3-yl or tetrahydropyran-4-yl, and physiologically hydrolyzable derivatives thereof having the hydroxy group in the 2 position of the 3-aminopropoxy side chain in esterified form.

Another group of compounds of the invention is the compounds of formula Ipb

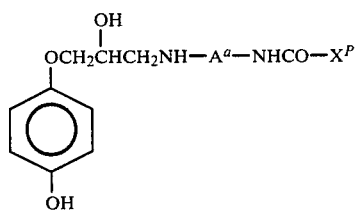

wherein $A^a$ and $X^p$ are as defined above.

In accordance with the invention a compound of the invention may be obtained by a process which includes the step of appropriately 3-amino-2-oxypropylating a corresponding compound of formula IV,

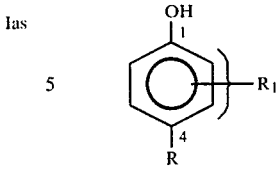

wherein R and $R_1$ are as defined above, or a precursor form thereof.

The process step of the invention may be effected in conventional manner for the production of analogous 3-amino-2-oxy-propoxyaryl compounds.

The choice of the most appropriate variant should, of course, take into account the reactivities of the substituents present.

When R is a group $-Z-(CH_2)_n-Y-R_2$ preferably a compound of formula IV is used, rather than a precursor form thereof.

A precursor form of a compound of formula IV is a compound capable of being converted into a compound of formula IV, e.g. by appropriate etherification, aromatic substitution and/or deprotection. Thus, when Z is oxygen, a precursor form is e.g. a corresponding compound wherein the moiety $-O-(CH_2)_{2,3}-Y-R_2$ is replaced by a hydroxy group, optionally in protected form. For those compounds wherein $R_2$ is other than hydrogen, a precursor form is e.g. a corresponding compound wherein the moiety $-Y-R_2$ is hydroxy or sulfhydryl, optionally in protected form. For those compounds wherein $R_2$ is hydrogen, a precursor form is e.g. a compound wherein the moiety $-Y-H$ is in protected form.

Thus, the process step of the invention may be effected in more than one stage. For example, a compound of formula IV in protected form may be used, or a 3-amino-3-oxypropyl moiety in protected form may be introduced, and subsequently, after the 3-amino-2-oxypropylation has been effected, any protecting group present may be split off.

Benzyl, methyl or 2-tetrahydropyranyl, preferably benzyl, are examples of a protecting group for e.g. a hydroxy-substituted phenyl ring.

In one form of the process according to the invention, the 3-amino-2-oxypropylation is effected in two main process stages.

In a first process stage a group $-CH_2-R_x$, wherein $R_x$ is a group capable of reacting with a primary amine to give a 2-amino-1-hydroxyethyl group, is introduced by O-alkylation in the 1-position into a compound of formula IV to give a corresponding compound of formula II,

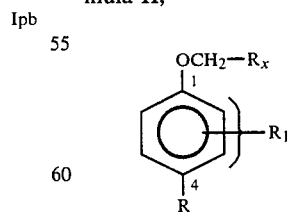

wherein $R_x$, $R_1$ and R are as defined above.

In a second process stage a compound of formula II is aminated with a corresponding compound of formula III, $$H_2N-A-NHCO-X \qquad \text{III}$$

wherein A and X are as defined above and, where required, at least one hydroxy group in a resultant compound of formula I is appropriately esterified.

The O-alkylation process stage in the 1 position may be effected in a manner known for the production of analogous ethers. A compound of formula IV preferably is reacted in anionic form. It may be indicated to use a compound of formula IV wherein any hydroxy group present other than the hydroxy group in the 1-position is in protected form.

The amination process stage may be effected in conventional manner for the production of analogous 3-amino-2-hydroxypropoxyaryl compounds. For example, $R_x$ may be a group of formula

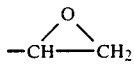

or a derivative of this group, e.g. a group of formula —CH(OH)—CH$_2$L, wherein L is chlorine, bromine or a group $R_y$—SO$_2$—O—, wherein $R_y$ is phenyl, tolyl or lower alkyl. L is especially chlorine. The reaction is preferably effected in ethanol or in an appropriate ether such as dioxane. Optionally an excess of the amine may be used as solvent. Alternatively the reaction may be effected in a fusion melt. Suitable reaction temperatures may be from about 20° to about 200° C., conveniently the reflux temperature of the reaction mixture when a solvent is present.

The optional esterification in a resultant compound of formula I may be effected in manner known for the production of analogous esters, if necessary using selective conditions when other reactive groups, e.g. hydroxy or amino, are present.

The compounds of the invention may exist in free form, i.e. normally as a base, or in salt form. Free forms of the compounds of the invention may be converted into salt forms, e.g. acid addition salt forms, and vice versa, in conventional manner. Suitable acids for acid addition salt formation include hydrochloric, malonic, succinic and fumaric acid.

In the compounds of the invention the carbon atom in e.g. the 2 position of the 3-aminopropoxy side chain is asymmetrically substituted. The compounds may thus exist in the racemic form or in individual optical isomer form. The preferred optical isomer has the S-configuration at this asymmetrically substituted carbon atom of the 3-aminopropoxy side chain. Individual optical isomer forms may be obtained in conventional manner, for example by using optically active starting materials or by fractional crystallization of racemate salts using optically active acids. Diastereoisomeric mixtures which may exist e.g. when X is tetrhydropyran-2- or -3-yl may also be separated in conventional manner, e.g. by fractional crystallization.

Insofar as the preparation of any particular starting material is not particularly described, this may be effected in conventional manner.

In the following Examples all temperatures are in degrees Centigrade and are uncorrected.

EXAMPLE 1

1-[4-(2-Methoxyethyl)phenoxy]-3-[2-(tetrahydropyran-3-ylcarbonylamino)ethylamino]-2-propanol 5 g of 1-(2,3-epoxypropoxy)-4-(2-methoxyethoxy)-benzene and 6 g of N-(2-aminoethyl)tetrahydropyran-3-carboxamide are heated together at 130° for 30 minutes. The mixture is allowed to cool and then dissolved in ethyl acetate and worked up in the usual manner. The title compound is obtained (M.P. 107°–108°—from methanol/ethylacetate).

The starting material is obtained by reacting 4-(2-methoxyethyl)phenol with epichlorhydrin in the presence of a catalytic amount of piperidine.

From the appropriate compounds of formula II wherein $R_x$ is

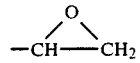

(unless indicated otherwise in the table) and the appropriate compounds of formula III the following compounds of formula I may be obtained in analogous manner to Example 1:

| Example No. | $R_1{}^a$ | X | R | A | | M.P. |
|---|---|---|---|---|---|---|
| 2 | H | tetrahydropyran-3-yl | —O(CH$_2$)$_2$OMe | —(CH$_2$)$_2$— | sc | 118–120° |
| 3 | H | tetrahydropyran-4-yl | —(CH$_2$)$_2$OMe | —(CH$_2$)$_2$— | b | 128–129° |
| 4$^b$ | o-Br | tetrahydropyran-4-yl | —(CH$_2$)$_2$Ome | —(CH$_2$)$_2$— | b | 118–127° |
| 5 | o-Br | tetrahydropyran-3-yl | —O(CH$_2$)$_2$OCH$_2$—◁ | —(CH$_2$)$_2$— | b | 105–107° |
| 6 | H | tetrahydropyran-4-yl | —O(CH$_2$)$_2$Ome | —(CH$_2$)$_2$— | b | 107–108,5° |
| 7$^c$ | o-CN | tetrahydropyran-4-yl | —(CH$_2$)$_2$OMe | —(CH$_2$)$_2$— | b | 128–130° |
| 8 | o-Br | tetrahydropyran-3-yl | —(CH$_2$)$_2$OMe | —(CH$_2$)$_2$— | b | 104–107° |
| 9 | o-CN | tetrahydropyran-3-yl | —(CH$_2$)$_2$OMe | —(CH$_2$)$_2$— | b | 118–122° |
| 10 | H | tetrahydropyran-3-yl | —O(CH$_2$)$_2$OCH$_2$—◁ | —(CH$_2$)$_2$— | b | 121–123° |
| 11 | H | tetrahydropyran-4-yl | —O(CH$_2$)$_2$OCH$_2$—◁ | —(CH$_2$)$_2$— | b | 106–108° |
| 12 | H | tetrahydropyran-4-yl | —O(CH$_2$)$_2$OCH$_2$—◁ | —(CH$_2$)$_3$— | b | 96–97° |
| 13$^d$ | H | tetrahydropyran-3-yl | OH | —(CH$_2$)$_2$— | b | 122–125° |

-continued

| Example No. | $R_1{}^a$ | X | R | A | | M.P. |
|---|---|---|---|---|---|---|
| 14$^c$ | H | tetrahydropyran-3-yl | OH | —(CH$_2$)$_2$— | b | 122–125° |
| 15$^d$ | H | tetrahydropyran-4-yl | OH | —(CH$_2$)$_2$— | b | 124–126° |
| 16$^e$ | H | tetrahydropyran-4-yl | OH | —(CH$_2$)$_2$— | b | 124–126° | b = in free base form
sc = in bis(base)succinate salt form
Me = methyl
M.P. = melting point
$^a$o- = in the position on the phenyl ring ortho to the 3-aminopropoxy side chain.
$^b$The intermediate 2-bromo-4-(2-methoxyethyl)phenol (oil) is obtained by bromination of 4-(2-methoxyethyl)phenol.
$^c$The intermediate 2-hydroxy-5-(2-methoxyethyl)benzonitrile(M.P. 94–96°) is obtained from 2-bromo-4-(2-methoxyethyl)phenol (see under $^b$) by reaction with benzyl bromide, cyanidation of the resultant derivative with CuCN and debenzylation of the resultant 2-benzyloxy-5-(2-methoxyethyl)benzonitrile (oil) with palladium on charcoal.
$^d$The amination step is effected in an inert atmosphere with the hydroxy group protected in the form of a benzyloxy group and the resultant protected compound thereafter deprotected by hydrogenation with palladium on charcoal.
$^e$Starting from the corresponding compound of formula II wherein $R_x$ is —CH(OH)CH$_2$Cl.

The following derivatives, esters of the compounds of formula I (which are compounds of formula E) may be obtained by appropriately esterifying the 2 position of the 3-aminopropoxy side chain in the corresponding compound of formula I (the other substituents are as for the corresponding compound of formula I):

| Example No. | Corresponding compound of formula I (Example No.) | $R_e$ (formula E) |
|---|---|---|
| 1-E | 1 | n-nonyl |
| 2-E | 1 | 3-ethylbenzyl |

The compounds of the invention are useful because they possess pharmacological activity in animals.

In particular, the compounds possess β-adrenoceptor blocking activity, as indicated by standard tests. For example, in the spontaneously beating guinea pig atrium (A. Bertholet et al., Postgrad. Med. J. 57, Suppl. 1 [1981], 9–17) they inhibit the positive chronotropic isoprenaline effect at bath concentrations of from about $10^{-7}$M to about $10^{-6}$M.

Thus, in the test above, the following compounds exhibit effective β-adrenoceptor blocking activity at the dose indicated below:

| Example No. | Guinea pig atrium test Effective dose (molar concentration) [M] |
|---|---|
| 3 | $2 \times 10^{-7}$ |
| 6 | $4 \times 10^{-7}$ |
| 7 | $8 \times 10^{-8}$ |
| 8 | $8 \times 10^{-8}$ |
| 9 | $3 \times 10^{-7}$ |
| 11 | $2 \times 10^{-7}$ |
| 12 | $3 \times 10^{-6}$ |
| Propranolol | $3 \times 10^{-9}$ |

The compounds are therefore useful as β-adrenoceptor blocking agents, e.g. for the prophylaxis and therapy of coronary diseases such as angina pectoris, conditions which are associated with sympathetic over-stimulation, e.g. nervous heart complaints, myocardial infarction, hypertension, for the intermediate treatment of migraine and for the treatment of glaucoma and thyreotoxicosis. In view of their antiarrhythmic effect they are useful as antiarrhythmics for the treatment of disturbances in the heart rhythm such as supraventricular tachycardia.

For these uses, the dose will, of course, vary according to the substance used, the mode of administration and the desired treatment. In general, however, satisfactory results are obtained with a daily dosage of about 0.1 mg to about 10 mg per kg body weight; administration may be effected in 2 to 4 divided doses or in sustained release form. For the larger mammal the total daily dosage is from about 10 mg to about 500 mg; suitable forms for oral administration generally contain from about 2.5 mg to about 250 mg of the compounds together with solid or liquid carriers and/or diluents.

An example of a dosage range is from about 20 mg to about 200 mg, preferably from about 50 mg to about 100 mg.

The compounds have more marked and wider spread beneficial pharmacological properties than could be expected for compounds having this type of structure. In particular, their activity is more cardioselective than could be expected from similar known compounds.

This can be demonstrated in vitro in tracheal preparations of the guinea pig which are prepared according to standard procedures in which a portion of the tracheal muscle is allowed to relax under the influence of isoproterenol and in the presence of known concentrations of the compound to be tested.

In this system potency in tracheal preparations with Examples 1 to 13 and 15 is less than in the atrium as determined above. In the case of Examples 6, 10 and 11 no effect is found in the trachea at concentrations as high as $1 \times 10^{-4}$M and for Example 1 at $2 \times 10^{-5}$M. By comparison propranolol exerts a blocking effect in this model at a concentration of $1 \times 10^{-8}$M.

In pithed rat preparations the compounds can produce a 100% inhibition of the effects of isoproterenol administered in the dose of 0.1 μg/kg i.v. on heart rate, but usually have no effect on the blood pressure response to isoproterenol. The dose required to inhibit the isoproterenol tachycardia by 50% ranges from 3 μg/kg to 300 μg/kg i.v.

In the conscious dog, the maximum inhibitory effect of the compounds of Examples 6 and 11 on the isoproterenol-induced tachycardia at a dose of isoproterenol of 0.1 μg/kg i.v. is from 50 to 60% of that obtainable with non-selective agents such as propranolol. The lack of complete blockade in the dog reflects the significant number of β$_2$ cardiac receptors in this preparation, which are not blocked by highly β$_1$-cardioselective compounds.

The high selectivity of blockade for these compounds is of major importance in the treatment of hypertension where exacerbation of an existing asthmatic condition may be precipitated by currently commercially available compounds.

The compounds also possess a degree of intrinsic sympathomimetic activity, a property which is useful in preventing undue bradycardia and helps reduce the incidence of heart failure in subjects with heart muscle disease. They also generally have a more favourable oral absorption than could be expected for compounds having this type of structure.

The compounds of the invention having a hydroxy substituent in the position para to the 3-aminopropoxy side chain have a considerable stimulating activity on cardiac β-receptors in addition to the β-adrenergic blocking activity, as indicated by standard tests. For example, in the anaesthetized, vagotonised cat spinalized at the level of the second cervical vertebra they exert an increase in cardiac contractile force at a dose of from about 20 to about 2500 μg/kg i.v., as measured with a strain gauge arch sewn onto the left ventricle. The effect may also be measured as a concentration-dependent stimulation of the isolated, spontaneously-beating guinea pig atrium. The magnitude of the stimulation is about 40 to 50% of the stimulation attainable with a standard β-stimulant such as isoproterenol.

These compounds therefore possess β-agonist as well as selective β-antagonist properties. They are useful as cardiotonics e.g. for the treatment of heart insufficiency, especially in situations where a positive inotropic effect is desired without significant influence on blood pressure. The balance between the agonistic and antagonistic activities is particularly favourable for these compounds; the agonistic component contributes the cardiotonic activity while the antagonistic component protects against an excessive increase in contractile force which might lead to arrhythmias.

For this cardiotonic use the dose will, of course, vary according to the substance used, the mode of administration and the desired treatment. In general, however, satisfactory results are obtained with a daily dosage of about 0.01 mg to about 10 mg per kg body weight; administration may be effected in 2 to 4 divided doses, or in sustained release form. For the larger mammal the total daily dosage is from about 1 mg to about 500 mg; suitable forms for oral administration generally contain from about 0.25 mg to about 250 mg of the compounds together with solid or liquid carriers and/or diluents.

Of the compounds of the invention in optically active form those in which the carbon atom in the 2-position of the 3-aminopropoxy side chain has the (S)-configuration are pharmacologically more active than the corresponding (R)-enantiomers.

The preferred uses of the compounds are the use against coronary diseases and hypertension.

Preferred are the compounds of Examples 6 and 11, especially of Example 11.

The compounds of the invention in free form or in the form of their pharmaceutically acceptable salts may be administered alone or in suitable dosage forms. The present invention also provides a pharmaceutical composition comprising a compound of the invention in free form or in salt, preferably acid addition salt form in association with a pharmaceutical carrier or diluent. Such forms, e.g. a solution or a tablet, may be produced according to known methods.

We claim:

1. A compound of the formula Ia,

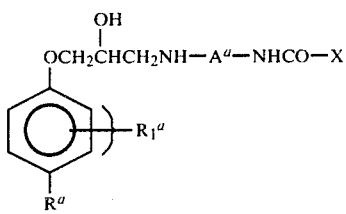

wherein
X is tetrahydopyranyl,
$A^a$ is alkylene of 2 to 5 carbon atoms,
$R_1^a$ is hydrogen, hydroxy, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, pyrrol-1-yl, cyano, carbamoyl, alkenyl of 2 to 5 carbon atoms, alkenyloxy of 3 to 5 carbon atoms wherein the double bond is not attached to the carbon atom adjacent to the oxygen atom, alkanoyl of 2 to 5 carbon atoms, nitro, amino, alkanoylamino of 1 to 5 carbon atoms or alkoxycarbonylamino of 1 to 4 carbon atoms in the alkoxy moiety thereof and
$R^a$ is hydroxy or a group $-Z-(CH_2)_n-Y-R_2^a$ wherein Y is an oxygen or sulfur atom and either Z is an oxygen atom and n is 2 or 3 or Z is a bond and n is 1, 2 or 3 and
$R_2^a$ is hydrogen, alkyl of 1 to 5 carbon atoms, alkenyl of 3 to 5 carbon atoms wherein the double bond is not attached to the carbon atom adjacent to Y, cycloalkyl of 5 to 7 carbon atoms, cycloalkylalkyl of 3 to 7 carbon atoms in the cycloalkyl moiety and of 1 to 4 carbon atoms in the alkyl moiety thereof, or phenyl, phenylalkyl of 7 to 10 carbon atoms or phenylalkenyl of 9 to 11 carbon atoms wherein the double bond is not attached to the carbon atom adjacent to Y, the last three substituents optionally being mono- or independently di- or independently trisubstituted in the phenyl ring by alkyl of 1 to 4 carbon atoms, alkoxy of 1 to 4 carbon atoms or halogen of atomic number of from 9 to 35,
or a pharmaceutically acceptable salt form thereof and physiologically hydrolyzable esters thereof.

2. A pharmaceutical composition for treatment of coronary diseases, hypertension, migraine or glaucoma comprising a pharmaceutically effective amount of a compound of claim 1 in free form or in pharmaceutically acceptable salt form, in association with a pharmaceutical carrier or diluent.

3. A method of treating coronary diseases, which comprises administering to a patient in need of such treatment a therapeutically effective amount of a compound of claim 1 in free form or in pharmaceutically acceptable salt form.

4. A method of effecting β-adrenoceptor blockade which comprises administering to a patient in need of such treatment a therapeutically effective amount of a compound of claim 1 in free form or in pharmaceutically acceptable salt form.

5. A compound of claim 1, wherein X is tetrahydropyran-3-yl or tetrahydropyran-4-yl.

6. A method of treating conditions associated with sympathetic overstimulation, which comprises administering to a patient in need of such treatment a therapeutically effective amount of a compound of claim 1 in free form or in pharmaceutically acceptable salt form.

7. A method of treating myocardial infarction, which comprises administering to a patient in need of such treatment a therapeutically effective amount of a compound of claim 1 in free form or in pharmaceutically acceptable salt form.

8. A method of treating hypertension, which comprises administering to a patient in need of such treatment a therapeutically effective amount of a compound of claim 1 in free form or in pharmaceutically acceptable salt form.

9. A method of treating migraine, which comprises administering to a patient in need of such treatment a therapeutically effective amount of a compound of claim 1 in free form or in pharmaceutically acceptable salt form.

10. A method of treating glaucoma, which comprises administering to a patient in need of such treatment a therapeutically effective amount of a compound of claim 1 in free form or in pharmaceutically acceptable salt form.

11. A method of treating thryeotoxicosis, which comprises administering to a patient in need of such treatment a therapeutically effective amount of a compound of claim 1 in free form or in pharmaceutically acceptable salt form.

12. A method of treating heart rhythm disorders, which comprises administering to a patient in need of such treatment a therapeutically effective amount of a compound of claim 1 in free form or in pharmaceutically acceptable salt form.

13. A compound of claim 1 of formula E

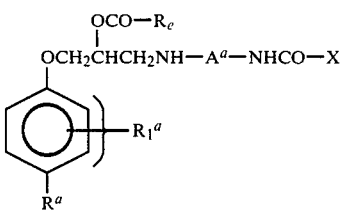

wherein $R^a$, $R_1^a$, $A^a$ and X are as defined in claim 1 and $R_e$ is alkyl of 1 to 12 carbon atoms, cycloalkyl of 3 to 7 carbon atoms, phenyl, phenylalkyl of 7 to 12 carbon atoms, or phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

14. A compound of claim 13, wherein $R^a$ is $OCOR_e$.

15. A compound of claim 13, wherein $R^a$ is —Z—$(CH_2)_n OCOR_e$.

16. A compound of claim 13, wherein $R_1^a$ is $OCOR_e$.

17. A compound of claim 1, of the formula I'a

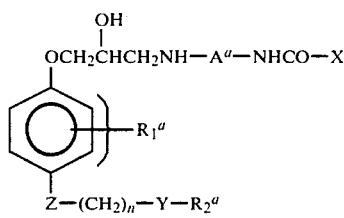

wherein $A^a$, X, Y, Z, n, $R_1^a$ and $R_2^a$ are as defined in claim 1, and the physiologically hydrolyzable esters thereof.

18. A compound of claim 17, wherein $R_2^a$ is hydrogen, alkyl of 1 to 4 carbon atoms, alkenyl of 3 to 5 carbon atoms wherein the double bond is not attached to the carbon atom adjacent to Y, cycloalkyl of 5 to 7 carbon atoms or cycloalkylalkyl of 3 to 7 carbon atoms in the cycloalkyl moiety and of 1 to 4 carbon atoms in the alkyl moiety thereof.

19. A compound of claim 1, wherein $R_1^a$ is hydroxy.

20. A compound of claim 1, of the formula I''

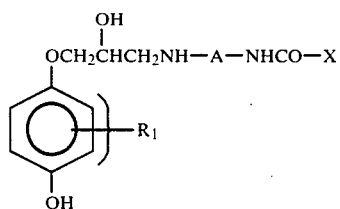

wherein A is as defined for $A^a$ in claim 1, $R_1$ is as defined for $R_1^a$ in claim 1 and X is as defined in claim 1, and the physiologically hydrolyzable esters thereof.

21. A compound of claim 1, of the formula Ias

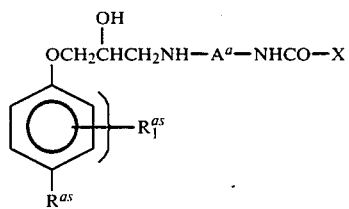

wherein X is as defined in claim 1, $A^a$ is alkylene of 2 to 5 carbon atoms, $R_1^{as}$ is hydrogen, halogen of atomic number of 9 to 53 or cyano and $R^{as}$ is hydroxy or a group —Z—$(CH_2)_n$—O—$R_2^{as}$, wherein Z and n are each as defined in claim 1, and $R_2^{as}$ is alkyl of 1 to 5 carbon atoms, cycloalkyl of 5 to 7 carbon atoms, or cycloalkylalkyl of 3 to 7 carbon atoms in the cycloalkyl moiety and of 1 to 4 carbon atoms in the alkyl moiety thereof.

22. A compound of claim 21, wherein $R_1^{as}$ is as defined in claim 21, and $R^{as}$ is the group —Z—$(CH_2)_n$—O—$R_2^{as}$, wherein Z, n and $R_2^{as}$ are as defined in claim 21.

23. A compound of claim 21, wherein $R_1^{as}$ is hydrogen and $R^{as}$ is hydroxy.

24. A compound of claim 5, wherein the hydroxy group in the two-position of the 3-aminopropoxy side chain is in esterified form.

* * * * *